(12) United States Patent
Inoue et al.

(10) Patent No.: US 8,915,120 B2
(45) Date of Patent: Dec. 23, 2014

(54) CHROMATOGRAPH DEVICE

(75) Inventors: Takashi Inoue, Kyoto (JP); Takeshi Maji, Kyoto (JP); Hirotaka Naganuma, Kusatsu (JP); Shinichi Mitsuhashi, Kyoto (JP); Yoshitaka Noda, Kyoto (JP)

(73) Assignee: Shimadzu Corporation, Kyoto-Shi (JP)

( * ) Notice: Subject to any disclaimer, the term of this patent is extended or adjusted under 35 U.S.C. 154(b) by 109 days.

(21) Appl. No.: 13/559,415

(22) Filed: Jul. 26, 2012

(65) Prior Publication Data

US 2014/0026757 A1    Jan. 30, 2014

(51) Int. Cl.
| | |
|---|---|
| *G01N 1/00* | (2006.01) |
| *G01N 35/10* | (2006.01) |
| *G01N 30/16* | (2006.01) |
| *G01N 30/24* | (2006.01) |
| *G01N 1/22* | (2006.01) |

(52) U.S. Cl.
CPC .... *G01N 35/1081* (2013.01); *G01N 2001/2229* (2013.01); *G01N 1/2226* (2013.01); *G01N 30/16* (2013.01); *G01N 30/24* (2013.01); *G01N 35/1095* (2013.01); *G01N 35/1083* (2013.01)
USPC ............... 73/23.41; 73/863.01; 73/863.11; 96/105

(58) Field of Classification Search
CPC .............. G01N 1/2226; G01N 1/4022; G01N 2001/2229; G01N 30/16; G01N 30/24; G01N 35/10; G01N 35/1081; G01N 35/1083; G01N 35/109; G01N 35/1095
USPC ................. 73/23.41, 863.01, 863.11, 864.91; 96/101, 105
See application file for complete search history.

(56) References Cited

U.S. PATENT DOCUMENTS 8,806,965 B2 * 8/2014 Sato et al. ................... 73/863.11
2011/0239792 A1 * 10/2011 Sato et al. ................... 73/863.11

FOREIGN PATENT DOCUMENTS

JP    2002-005913    1/2002

* cited by examiner

*Primary Examiner* — Robert Clemente
(74) *Attorney, Agent, or Firm* — Bingham McCutchen LLP

(57) ABSTRACT

A vial feed device is equipped with a feed arm, which is positioned between a vial tray and an oven and below either of them and having a feeding housing unit and a cooling housing unit, and a vial up-and-down moving mechanism for placing and removing vials in and from vial tray and oven. Feed arm is rotationally driven by a drive motor to move a feeding housing unit, a cooling housing unit and up-and-down moving mechanism toward vial tray or oven. High-temperature vials in oven are housed in cooling housing unit until cooling time T elapses. After cooling time T elapses, cooling housing unit is moved to a lower part of vial tray by feed arm, to be returned to vial tray by up-and-down moving mechanism.

3 Claims, 4 Drawing Sheets

US 8,915,120 B2

CHROMATOGRAPH DEVICE

TECHNICAL FIELD

The present invention relates to a chromatograph device and, in particular, to a specimen container-feeding device for transporting multiple specimen containers between a specimen container tray and a heating device for introducing specimen containers holding liquid specimens or solid specimens into a gas chromatograph device and the like so that specimen gas obtained by volatilization of the liquid specimen or solid specimen can be analyzed by a head space analysis method.

BACKGROUND ART

With a head space analysis method, a liquid specimen or a solid specimen that is contained in a container (vial) is heated for a predetermined amount of time at a predetermined temperature to volatize predetermined components in a specimen, and a certain amount of gas that includes the volatile components is collected from the head space at the top of the container and is led into a gas chromatograph device and the like. With the headspace analysis method, prior to collecting a gas (specimen gas) that contains the volatile components from the container, a pre-process is performed wherein the vial is placed in an oven and the specimen in the vial is heated (see Patent Literature 1).

Because the higher the heating temperature of the vials, the more efficiently the various volatile components can be extracted, a trend seen in recent years is to increase the heating temperature of the vials. After the heating temperature of the vials is increased and the analysis is completed, the vials are returned to the container holding unit while the vials are still hot. Because workers are free to place the vials in the container-holding unit during the analysis, there is a risk that a worker may inadvertently touch a hot vial.

Patent Literature 1: Unexamined Patent Application Publication No. 2002-5913

SUMMARY OF THE INVENTION

The problem to be solved by the present invention is to provide a chromatograph device wherein contact between a worker and a specimen container that is heated to a high temperature for head space analysis is prevented to the maximum extent possible.

Means for Solving the Problem

The chromatograph device according to the present invention that was made to solve the afore-described problem includes: a specimen container tray for holding a plurality of specimen containers; a heating device for housing and heating the specimen containers; and a container-feeding device for transporting the specimen containers from the specimen container tray to the heating device; wherein: the container-feeding device includes: a heated container storage unit for storing the specimen containers; a first container moving unit for moving the specimen containers from the heating device to the heated container storage unit; a heated container-feeding unit for transporting the heating container storage unit from a location close to the heating device to a location close to the specimen container tray; a second container movement unit for moving the specimen containers from the heated container storage unit to the specimen container tray; and a controller for controlling the first container moving unit, the heated container-feeding unit and the second container movement unit; and the controller controls the first container moving unit, the heated container-feeding unit and the second container movement unit so that the specimen containers are moved from the heated container storage unit to the specimen container tray after the specimen containers that are stored in the heated container storage unit have cooled to a normal temperature.

According to the present invention, the specimen containers that are moved from the heating device to the heated container storage unit are kept and stored in the heated container storage unit until they have cooled to a normal temperature and are not returned to the specimen container tray until then. Because of this the possibility of a worker inadvertently touching a hot specimen container is eliminated. Furthermore, because hot specimen containers are cooled to a normal temperature while they are stored in the heated container storage unit of the container-feeding device, the specimen containers do not obstruct the analysis of other specimens in the specimen container.

DETAILED DESCRIPTION OF THE INVENTION

Figure 1:
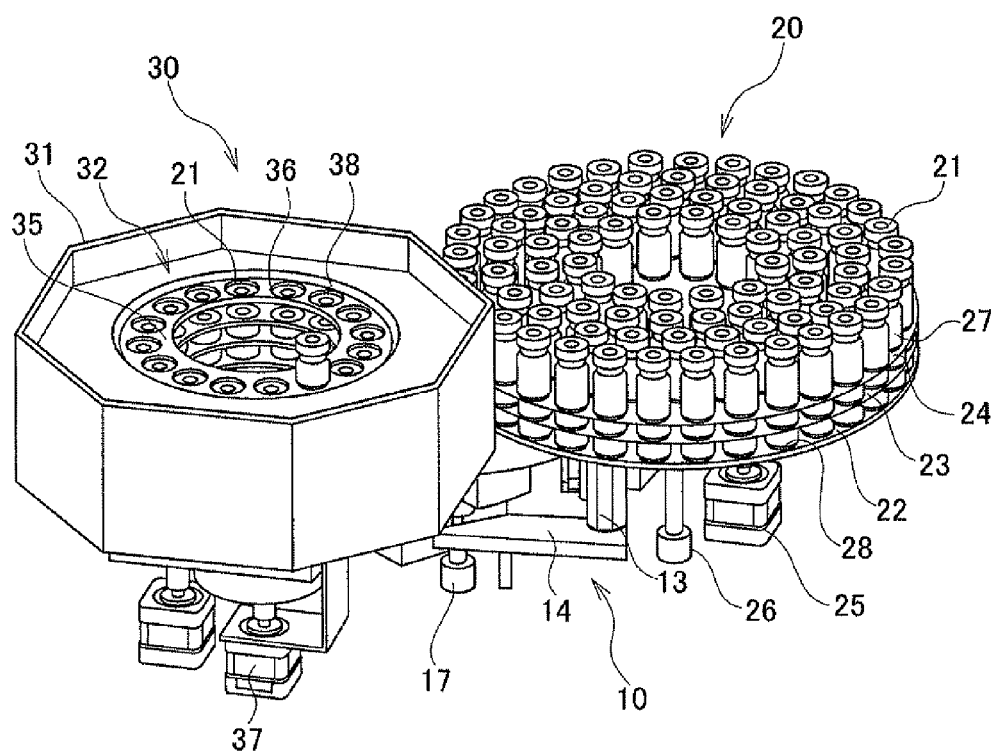
FIG. 1 is a perspective view showing the positional relationship among the feed device, vial tray and the oven in one embodiment of a chromatograph device according to the present invention.
Figure 2:
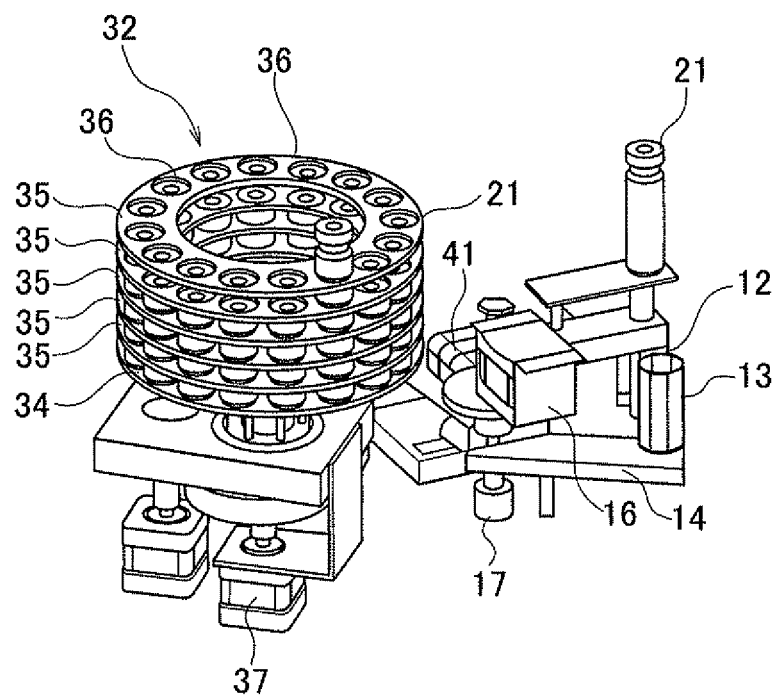
FIG. 2 shows a perspective view of the oven and the feed device.
Figure 3:
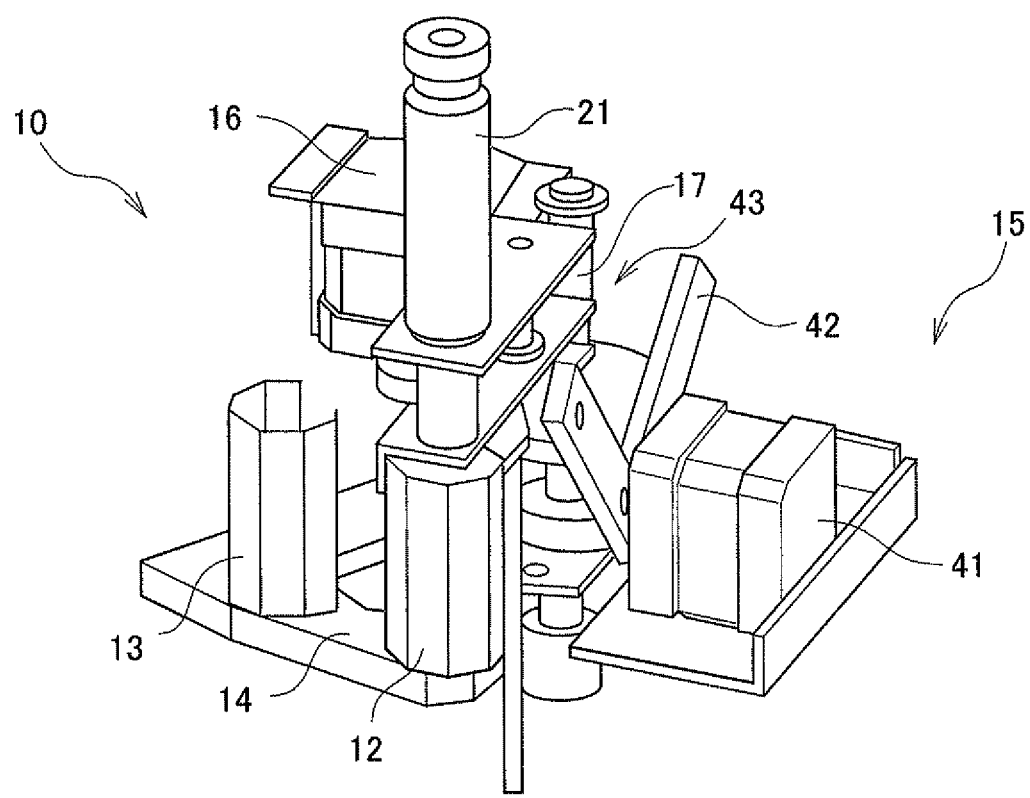
FIG. 3 shows a perspective view of the overall configuration of the feed device.

One embodiment of a chromatograph device according to the present invention is described next with reference to figures. The vial feed device according to the present embodiment is a device that transports vials that are held on a vial tray to an oven serving as a heating device as a preprocess for heating the vials (specimen containers) containing liquid specimens or solid specimens prior to introducing the specimens into a gas chromatograph device. In addition to vial feed device 10, FIG. 1 shows vial tray 20 and oven 30. The vial feed device 10 and vial tray 20 form a part of the chromatograph device and are housed within the enclosure of the chromatograph device.

The vial tray 20, which is where vials 21 are loaded in advance by a user, comprises a disk-shaped base plate 22 and two disk-shaped holding plates 23 and 24, which are placed some distance apart from each other. The two holding plate 23 and 24, which are connected by a plurality of shaft members that are not illustrated, are rotationally driven about a rotation axis 26 by a drive motor 25. A plurality of holes 27 whose size is just large enough to snugly accommodate vials 21 is formed as four concentric rings.

A plurality of concave regions 28 is formed on base plate 22 to correspond to holes 27 formed in holding plate 23 and 24. The holding plate 23 and 24 are rotationally driven in predetermined angular increments so that the bottom of the vials 21 held in each hole 27 is positioned within the concave regions 28. With the present embodiment, because the bottom of each vial 21 is spherical, the bottom of each vial 21 can be easily withdrawn from the concave regions 28 as the holding plate 23 and 24 are rotated. Furthermore, formed at a specific location of base plate 22 are openings (not illustrated) through which vials are raised and lowered. A total of four such openings through which vials are raised and lowered is formed so that each of the four concentric rings of concave regions 28 is provided with one such opening. The openings are usually covered by a shutter 29 (see FIG. 4).

Figure 4:
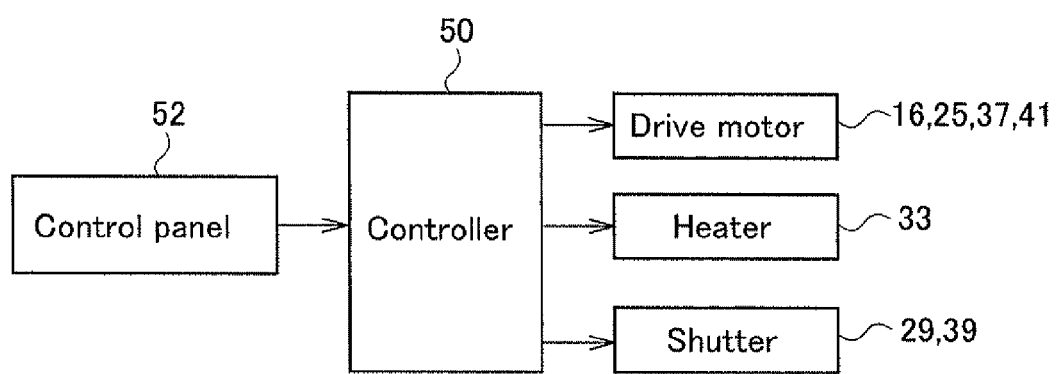
FIG. 4 is a block diagram showing the electrical configuration of the feed device.

Oven 30 includes: an octagonal cylindrical container 31; vial holding unit 32, which is housed within container 31; and a heater 33 for heating the interior of oven 30 (see FIG. 4). Even though no detailed illustration is provided, heater 33 is positioned at the center of vial holding unit 32 and can heat the interior of container 31 to, for example, 300° C. The vial holding unit 32 includes a disk-shaped base plate 34 and five annular holding plates 35. The five holding plates 35, which are connected by connecting shafts 36 to be parallel to and equidistant from each other, are rotated by drive motor 37. Formed on each holding plate 35 is a plurality of vertically aligned holes 38 just large enough to snugly accommodate vials 21.

A plurality of concave regions is formed on base plate 34 to correspond to holes 38 formed in the holding plates 35. Formed in one of the concave regions is an opening (not illustrated) through which vials are raised and lowered. The opening in oven 30 through which vials are raised and lowered is also usually covered by a shutter 39 (see FIG. 4), just as with the vial tray 20.

The top surface of container 31 is illustrated as if an opening is formed therein. This is solely for the purpose of making the internal structure visible. With the actual container 31, the top surface is completely sealed.

The vial feed device 10, which is positioned below the vial tray 20 and oven 30, includes: a feed arm 14 comprising feeding housing unit 12 and cooling housing unit 13; and a vial up-and-down moving mechanism 15 for inserting and removing a vial 21 into and from vial tray 20 and oven 30. The feed arm 14 is rotationally driven about rotation axis 17 by drive motor 16. The rotation of feed arm 14 causes the feeding housing unit 12, cooling housing unit 13 and up-and-down moving mechanism 15 to be moved to either the vial tray 20 side or the oven 30 side.

The vial up-and-down moving mechanism 15 comprises: a V-shaped rotating member 42 that is rotated by a drive motor 41 and a lifting/lowering member 43 that is raised and lowered by the rotating member 42. As further described below, the shutters are opened when the up-and-down moving mechanism 15 of the lifting/lowering member 43 is raised up to the opening formed in vial tray 20 or oven 30 through which vials are raised and lowered.

As FIG. 4 shows, the operation of drive motors 16, 25, 37 and 41, heater 33 and shutters 29 and 39 is controlled by a controller 50 that includes a CPU. The control panel 52 is used for setting various conditions, such as the temperature inside oven 30, vial heating time, vial cooling time, analysis period and the amount of the specimen to be sampled. While no vial 21 is being inserted or removed by the up-and-down moving mechanism 15 through the opening for raising and lowering the vials 21, the openings in vial tray 20 and oven 30 are covered by shutters 29 and 39.

Described next is the series of operations engaged in by the vial feed device 10 in the afore-described configuration for acquiring a vial 21 from vial tray 20, feeding the vial to oven 30 and then returning the vial to vial tray 20 after the vial is heated in the oven.

After vials 21 containing the specimen liquid are loaded in the vial tray 20, the operator sets the appropriate conditions and instructs the operation to begin. Alternatively, the start of analysis can be instructed in accordance with a time schedule that is set in advance. When either occurs, the feeding process of the vials 21 is started under the control of controller 50.

First, the drive motor 25 is started. This rotates holding plate 23 and 24 of vial tray 20, which causes a desired vial 21 to move to a position above the opening through which vials are raised and lowered.

Next, drive motor 16 is started. This rotates feed arm 14, which causes feeding housing unit 12, cooling housing unit 13 and up-and-down moving mechanism 15 to move to the vial tray 20 side. At this time, feeding housing unit 12 is positioned below the opening through which vials are raised and lowered.

Next, drive motor 41 is started. This rotates rotating member 42, which causes lifting/lowering member 43 to be lifted up to the lower surface of the opening through which vials are raised and lowered of vial tray 20. The shutter is next opened, and the lifting/lowering member 43 is lowered in synchrony with this. The result is for the vial 21 to be lowered together with the lifting/lowering member 43 into the feeding housing unit 12 where it is stored.

The drive motor 16 is then started. This rotates the feed arm 14, which causes the feeding housing unit 12, cooling housing unit 13 and up-and-down moving mechanism 15 to be moved to the oven 30 side. At this time, the feeding housing unit 12 is positioned below the opening of oven 30 through which vials are raised and lowered. When the drive motor of the up-and-down moving mechanism 15 starts, the lifting/lowering member 43 is raised, the shutter is opened, and the vials 21 that are stored in the feeding housing unit 12 are held by the vial holding unit 32 of oven 30.

The vials 21 that are held in the vial holding unit 32 of oven 30 are heated to a predetermined temperature by heater 33 and specimen gas is collected from the upper space region by a sampling device not illustrated. The specimen gas that is collected is injected into the specimen vaporization chamber of the gas chromatograph device where it is analyzed. When the collection of specimen gas from vial 21 is completed, the drive motor 16 is started, causing the feed arm 14 to rotate and the feeding housing unit 12, cooling housing unit 13 and up-and-down moving mechanism 15 to move to the oven 30 side. When this happens, the cooling housing unit 13 is positioned below the opening of oven 30 through which vials are raised and lowered. Next, the vials 21 inside the oven 30 are lowered by the up-and-down moving mechanism 15 and are stored in the cooling housing unit 13.

Once the vials 21 are placed in the cooling housing unit 13, controller 50 starts counting elapsed time t. Once the elapsed time t reaches the cooling time T set in advance, the feed arm 14 is driven and the cooling housing unit 13 is moved below the opening of vial tray 20 through which vials are raised and lowered. The up-and-down moving mechanism 15 then returns the vials 21 to vial tray 20. The cooling time T is set to a time sufficient for the vials 21 heated in oven 30 to be cooled to normal temperature.

Even if vials 21 are stored in the cooling housing unit 13, the vial feed device 10 uses the feeding housing unit 12 to transport vials 21 from the vial tray 20 to oven 30 according to a preset time schedule.

As afore-described, with the present embodiment, the vials that are moved from oven 30 to cooling housing unit 13 are held and stored in cooling housing unit 13 until preset cooling time T has elapsed to cool the vials. This means that a worker will not come into contact with vials 21 that are hot. In particular, with the present embodiment, because the feed device 10 is positioned below vial tray 20 and oven 30, contact between a worker and vials 21 that are hot is reliably prevented.

Furthermore, because vials 21 are placed in and removed from oven 30 through an opening that is formed in the bottom portion of oven 30, hot air that is in oven 30 is prevented from leaking outside to the maximum extent possible, thus suppressing the drop in temperature within oven 30 caused by the ingress and egress of vials 21.

Furthermore, with the present embodiment, because a single feed arm 14 comprises feeding housing unit 12 and cooling housing unit 13, vials 21 at a high temperature can be transported from vial tray 20 to oven 30 even while the hot vials 21 are being cooled.

However, in a situation where it is not necessary to transport the vials 21 from the vial tray 20 to the oven 30 while the vials 21 at a high temperature are being cooled, the single feed arm 14 can be configured to have only one housing unit, which has the combined use of the feeding housing unit 12 and the cooling housing unit 13.

The present invention is not limited to the afore-described embodiment and can be modified, for example, as follows.

A cooling device such as a fan can be positioned close to the transportation path of the specimen containers leading from the heating device to the specimen container tray. A cooling housing unit in which hot specimen containers are stored can be placed near the cooling device.

Furthermore, the holding plates 23, 24 provided in the vial tray 20, and the vial holding unit 32 having a disk holding plate situated in the oven 30 are not limited to a structure having multiple plates but can be a structure having one component formed, for example, by resin.

DESCRIPTION OF THE NUMERICAL REFERENCES

10. Vial feed device
12. Feeding housing unit
13. Cooling housing unit (heated container storage unit)
14. Feed arm
15. Vial up-and-down moving mechanism (first container moving unit, second container movement unit)
16, 25, 37, 41. Drive motor
20. Vial tray
21. Vial (specimen container)
22. Base plate
23 and 24. Holding plate
25. Drive motor
27. Opening through which vials are raised and lowered
30. Oven
31. Container
32. Vial holding unit
33. Heater
50. Controller

What is claimed is:

1. A chromatograph device comprising:
a specimen container tray for holding a plurality of specimen containers;
a heating device for housing and heating the specimen containers; and
a container-feeding device for transporting the specimen containers from the specimen container tray to the heating device and vice versa;
wherein:
the container-feeding device comprises:
a feed arm having a flat arm structure, positioned lower than the specimen container tray or the heating device to be moved between the two;
a cooling housing unit provided on the feed arm, for storing one of the specimen containers;
a first container moving unit provided to the feed arm, for lowering one of the specimen containers from the heating device into the cooling housing unit disposed below the heating device;
a second container moving unit provided to the feed arm, for raising the specimen container to the specimen containing tray from the cooling housing unit that is moved below the specimen containing tray by the feed arm;
a feeding housing unit provided on the feed arm adjacent to the cooling housing unit, for storing the specimen containers, wherein the second container movement unit moves one of the specimen containers from the specimen container tray to the feeding housing unit, and the feed arm is then moved to place the feeding housing unit below the heating device for the first container movement unit to raise the specimen container into the heating device;
a controller for controlling the first container moving unit, the feed arm, and the second container movement unit, wherein the controller controls the first container moving unit, the feed arm, and the second container movement unit so that the specimen containers are moved one by one from the cooling housing unit to the specimen container tray after the specimen containers that are stored in the cooling housing unit have cooled to a normal temperature.

2. The chromatograph device according to claim 1 wherein the feed arm is positioned lower than either the specimen container tray or the heating device, the second container moving unit obtains the specimen container from a lower part of the heating device and moves the specimen container to the cooling housing unit, and the first container movement unit moves specimen container from a lower part of the specimen container tray to the specimen container tray.

3. The chromatograph device according to claim 1, wherein the feed arm further comprises a cooling device for cooling the specimen container that is stored in the cooling housing unit.

* * * * *